United States Patent
Van Lancker

(10) Patent No.: US 9,493,850 B2
(45) Date of Patent: Nov. 15, 2016

(54) PROCESS FOR EXTRACTION OF PENTOSE FROM LIGNO-CELLULOSIC SUBSTRATE

(75) Inventor: Frank Van Lancker, Aalst (BE)

(73) Assignee: SYRAL BELGIUM NV, Aalst (BE)

( * ) Notice: Subject to any disclaimer, the term of this patent is extended or adjusted under 35 U.S.C. 154(b) by 0 days.

(21) Appl. No.: 14/373,284

(22) PCT Filed: Jan. 31, 2012

(86) PCT No.: PCT/EP2012/000411
§ 371 (c)(1),
(2), (4) Date: Jan. 13, 2015

(87) PCT Pub. No.: WO2013/113323
PCT Pub. Date: Aug. 8, 2013

(65) Prior Publication Data
US 2015/0114386 A1    Apr. 30, 2015

(51) Int. Cl.
C13K 13/00 (2006.01)
C07H 3/02 (2006.01)
C07H 1/08 (2006.01)
B01J 39/04 (2006.01)

(52) U.S. Cl.
CPC ............ C13K 13/007 (2013.01); B01J 39/043 (2013.01); C07H 1/08 (2013.01); C07H 3/02 (2013.01); C13K 13/002 (2013.01)

(58) Field of Classification Search
None
See application file for complete search history.

(56) References Cited

U.S. PATENT DOCUMENTS

| | | | |
|---|---|---|---|
| 4,025,356 A * | 5/1977 | Nyman et al. | 127/1 |
| 4,075,406 A | 2/1978 | Melaja et al. | |
| 4,329,183 A * | 5/1982 | Rousseau et al. | 127/46.2 |
| 5,244,553 A | 9/1993 | Goldstein | |
| 5,407,580 A | 4/1995 | Hester et al. | |
| 5,560,827 A | 10/1996 | Hester et al. | |
| 5,628,907 A * | 5/1997 | Hester et al. | 210/635 |
| 7,077,953 B2 | 7/2006 | Ranney | |
| 7,109,005 B2 * | 9/2006 | Eroma et al. | 435/158 |
| 2003/0154975 A1 * | 8/2003 | Lightner | 127/37 |
| 2009/0176286 A1 * | 7/2009 | O'Connor et al. | 435/139 |

FOREIGN PATENT DOCUMENTS

| | | |
|---|---|---|
| CN | 1477107 A | 2/2004 |
| CN | 101392009 A | 3/2009 |
| CN | 101705313 A | 5/2010 |
| EP | 219136 A2 | 4/1987 |
| GB | 922685 A | 4/1963 |
| WO | WO 9103574 A1 * | 3/1991 |
| WO | 9906133 A1 | 2/1999 |
| WO | 9910542 A1 | 3/1999 |
| WO | 2007048879 A1 | 5/2007 |

OTHER PUBLICATIONS

International Search Report dated Mar. 13, 2012.

* cited by examiner

Primary Examiner — Melvin C Mayes
Assistant Examiner — Stefanie Cohen
(74) Attorney, Agent, or Firm — Symbus Law Group, LLC; Clifford D. Hyra

(57) ABSTRACT

A process for the hydrolysis of xylose/arabinose-containing polymers, present in biomass material. The hydrolysis is performed by acid which is generated via salts present in the substrate, and whereby acid is constantly recycled, thereby strongly reducing salt discharge.

8 Claims, 5 Drawing Sheets

(1) conductivity
(2) Brix
(3) Monomeric Xylose (1) conductivity
(2) Brix
(3) Monomeric Xylose (1) conductivity
(2) Brix
(3) Monomeric Xylose

PROCESS FOR EXTRACTION OF PENTOSE FROM LIGNO-CELLULOSIC SUBSTRATE

FIELD OF THE INVENTION

The present invention relates to a process for the extraction of pentose from a ligno-cellulosic substrate, in particular a hemicellulose containing substrate. The invention relates in particular to a process for the extraction of an aldopentose, in particular xylose or arabinose from a ligno-cellulose (hemicellulose) containing substrate.

BACKGROUND

From the past quite some literature is available regarding the extraction of pentose sugars such as xylose and arabinose, from hemicellulose-containing substrates. Xylose thus extracted can be used as such, but it is mainly converted into xylitol or furfural. Arabinose can also be converted into furfural, or further processed into arabitol and/or hydrocracking products. Xylose and/or arabinose can be obtained from a broad range of substrates including by-products obtained during processing of agricultural or forestry raw materials. Typical examples of such by-products are e.g. cereal straw, cereal bran, corn stover, corn cobs, bagasse, sugarbeet pulp, almond shells, coconut shells, or other ligno-cellulosic by-products. This list should not be considered as limiting.

The majority of the prior art processes are using relatively mild acid conditions for hydrolysing hemicellulose, xylan or arabinoxylan structures present in these materials.

The thus obtained pentose solutions may contain quite some mineral and other impurities. When e.g. xylose is used as a substrate for preparing xylitol, these impurities have to be removed in order to obtain xylose solutions which can then be subjected to crystallisation, in view of obtaining high purity xylose.

In order to obtain the required degree of purity, various methods have been described, such as filtration in order to remove particulate impurities, ultrafiltration, ion exchange, decolouring, ion exclusion or chromatography, or combinations thereof (WO2007048879, p. 1, lines 23-27).

As a result of all these purification steps, side streams containing acids, salts and other organic impurities are obtained, which have to be disposed off. As disposal of these side streams becomes more and more expensive, while these side streams are considered as environmentally not desirable, there is a need to limit such side streams, and where possible to re-utilise them in the process.

Several attempts have already been made in order to limit waste streams during refining of xylose/arabinose-containing hydrolysates. Thereby several approaches were used.

One way of reducing waste streams during hemicellulose hydrolysis is by recovering and re-using acid for the hydrolysis of the hemicellulose-containing substrate. In EP219136 acid recovery from a pentose-containing solution is realised by means of a solvent extraction process, while in GB922685 hydrochloric acid is recovered via reduced pressure evaporation of an acidic pentose solution.

In U.S. Pat. No. 5,560,827 and U.S. Pat. No. 5,407,580, a process is disclosed using ion exclusion technology to separate a strong acid from non-ionic components such as sugar. Thereby the acid stream can be re-concentrated and re-used in the hydrolysis step. This reduces the undesirable production of huge quantities of waste gypsum. Strong acid cation exchange resins are used in these processes. The acid stream thus obtained does also contain other positively charged ions. When conducting such a process, there is observed that the separation efficiency between acid and sugars could be subject to improvement with regard to recovery and purity of pentose sugars and acid fractions.

Also in WO9906133 a method is disclosed for separating acid and sugars, obtained from the hydrolysis of ligno-cellulosic material. Thereby ion exclusion chromatography is used to recover and re-use part of the acid, thus reducing acid consumption. In this case a strong base anion exchange resin is used. Thereby, a more pure acid fraction is recovered containing less contaminants such as heavy metals and/or alkali and/or earth alkali metal ions. Compared to acid separation using cation resins in H+ form (U.S. Pat. No. 5,560,827 and U.S. Pat. No. 5,407,580), this option however is less favourable with respect to resin stability.

Recovery of acid also can be realised by means of electro dialysis. Such methods have been disclosed in several patent documents, such as U.S. Pat. No. 5,244,553, CN1477107 and CN101705313.

A third way of recovering acid from a sugar-containing stream is by means of nanofiltration. Such a process is disclosed in U.S. Pat. No. 7,077,953.

Also combinations of technologies are described, thereby focusing on the reduction of waste streams and/or the re-utilisation of acid streams. In the case of CN101392009, an acidic xylose solution is first submitted to a electrodialysis step whereby part of the sulphuric acid is recovered. The remaining stream is then further processed by means of ion exchange (cation/anion exchange sequence followed by mixed bed) and a final nanofiltration step. Thereby applicant states that waste acid and waste alkali are recovered during regeneration of the ion exchange resins, which saves on sulphuric acid consumption and avoids environmental pollution.

In U.S. Pat. No. 4,025,356 a process for the continuous hydrolysis of hemicellulose-containing material is disclosed, whereby at least two portions of the hydrolysate are recycled into the hydrolysis vessel. The first portion is quite concentrated in acid, the second weakly acid portion is obtained by washing the fibrous residue and is re-acidified before introducing it in the continuous hydrolysis vessel. Purpose of the process is to reduce acid consumption.

WO 99/10542 A1 relates to a method of preparing crystalline L-arabinose by extraction of sugar beet pulp, from which sugar has been extracted, in a strong alkaline solution, by hydrolysis of the obtained crude araban with a strong acid at an elevated temperature, by neutralization and filtration of the obtained solution, by chromatographic separation of the L-arabinose fraction, by purification of the obtained L-arabinose solution by means of cation and anion exchangers and adsorbent resins, and by recovering the pure L-arabinose as a crystalline product.

U.S. Pat. No. 4,075,406 describes a method for recovering xylose from pentosan-, preferably xylan-containing raw materials including the steps of hydrolyzing the raw material, purifying the hydrolysate by ion exclusion and color removal, and then subjecting the purified solution to chromatographic fractionation to provide a solution containing a high level of xylose.

Therefore with regard to the acid hydrolysis of pentose-containing polymers present in agricultural and forestry by-products, and the recovery of these pentose sugars, there still is a need for further reducing the formation of waste and the consumption of chemicals during this process. In addition, there is also a need for improving the performance of the processing steps with regard to the recovery of the pentoses and the acid.

SUMMARY

The purpose of the invention is obtained by providing a process for extraction of pentose from a ligno-cellulose containing substrate, wherein the process comprising the subsequent steps of:
- submitting the ligno-cellulose containing substrate to an acidic partial hydrolysis step in a hydrolysis reactor;
- separating the partially hydrolysed ligno-cellulose substrate into an insoluble fraction and a liquid fraction comprising dissolved minerals and water-soluble organic material;
- submitting the liquid fraction to a decationisation step, wherein said liquid fraction is sent over a strong-acid cation exchange (SACE) resin in the hydrogen form;
- subsequently sending the decationised liquid phase over a strong-acid cation exchange (SACE) resin working in an ion exclusion mode, wherein acid and neutral monomeric sugars are separated from each other; and
- recycling at least a part of the acid to the hydrolysis reactor.

The ligno-cellulose containing substrate, is in particular a hemicellulose containing substrate.

The solution proposed by the present invention is based on the idea of effectively using the mineral salts present in the substrate, as the source for the acid that is used to hydrolyse pentose-containing polymers. As a result thereof, mineral acid consumption will be reduced to a minimum and as a consequence thereof, also the disposal of waste salt. In addition, it was surprisingly found that the recovery of pentose sugars and acid is clearly improved, this as the result of the specific processing steps being part of the invention.

In a preferred process according to the invention said acidic partial hydrolysis step is conducted at a pH of from 0.5 to 2. Preferably between a pH between 1 and 2. Preferably, in said acidic partial hydrolysis step, the reaction temperature varies between 70° C. and 140° C., preferably between 80° C. and 120° C., and more preferably between 90° C. and 110° C.

In a more preferred process according to the invention, said acidic partial hydrolysis step is conducted in batch or continuously. Performing the hydrolysis step continuously is preferred. Preferably, in a continuously performed hydrolysis step, the recycled acid is added counter-currently or co-currently to the hydrolysis reactor.

According to an advantageous process according to the invention the separated insoluble fraction is further washed and pressed, wherein the wash water is returned into the hydrolysis reactor. Thereby residual acid and soluble organic material is recovered and recycled into the hydrolysis reactor.

In a particular process according to the invention prior to the decationisation step, said liquid fraction is concentrated until about 25-50% d.s. Preferably, concentration is realized by evaporation, using the known standard methods. Equipment for evaporation can be selected among plate evaporators, falling film, multiple effect, rising film, or forced circulation evaporators, a falling film evaporator being preferred.

In a preferred process according to the invention said liquid fraction is sent over a strong-acid cation exchange (SACE) resin, working in a decationisation mode, at a velocity of 0.1 to 10 BV/h and at a temperature of between 40° C. and 99° C. In a more preferred embodiment, decationisation is realised at a temperature of between 40 and 60° C. respectively between 80 and 99° C. (hydrolysis of pentose polymers redundant respectively desirable), and at a percolation speed of 0.5 to 5 BV/h.

During this decationisation step minerals extracted from the substrate are transformed into acid, thus providing acid generated from the substrate. At the same time alkali- and earth alkali-metals, heavy metals such as iron or chromium, and nitrogen-containing substances are removed, providing an acid stream low in cations.

According to a more preferred process in accordance with the invention the strong-acid cation exchange (SACE) resin, working in a decationisation mode, is regenerated using a part of the acid obtained during the ion exclusion step. This regeneration step results in a waste stream which is then purged of. This quantity of acid is compensated by a quantity of make-up acid. In a most preferred process according to the invention, make-up acid is added to the hydrolysis reactor and/or used for the regeneration of the strong-acid cation exchange (SACE) resin, working in a decationisation mode.

BRIEF DESCRIPTION OF THE DRAWINGS

This invention will now be described in more detail and illustrated by the following graphs and examples which should be considered as being not limiting to the scope of the invention as such and as expressed in the following claims, wherein reference numerals are used to refer to the attached drawings, wherein

DETAILED DESCRIPTION OF EMBODIMENTS

Figure 1:
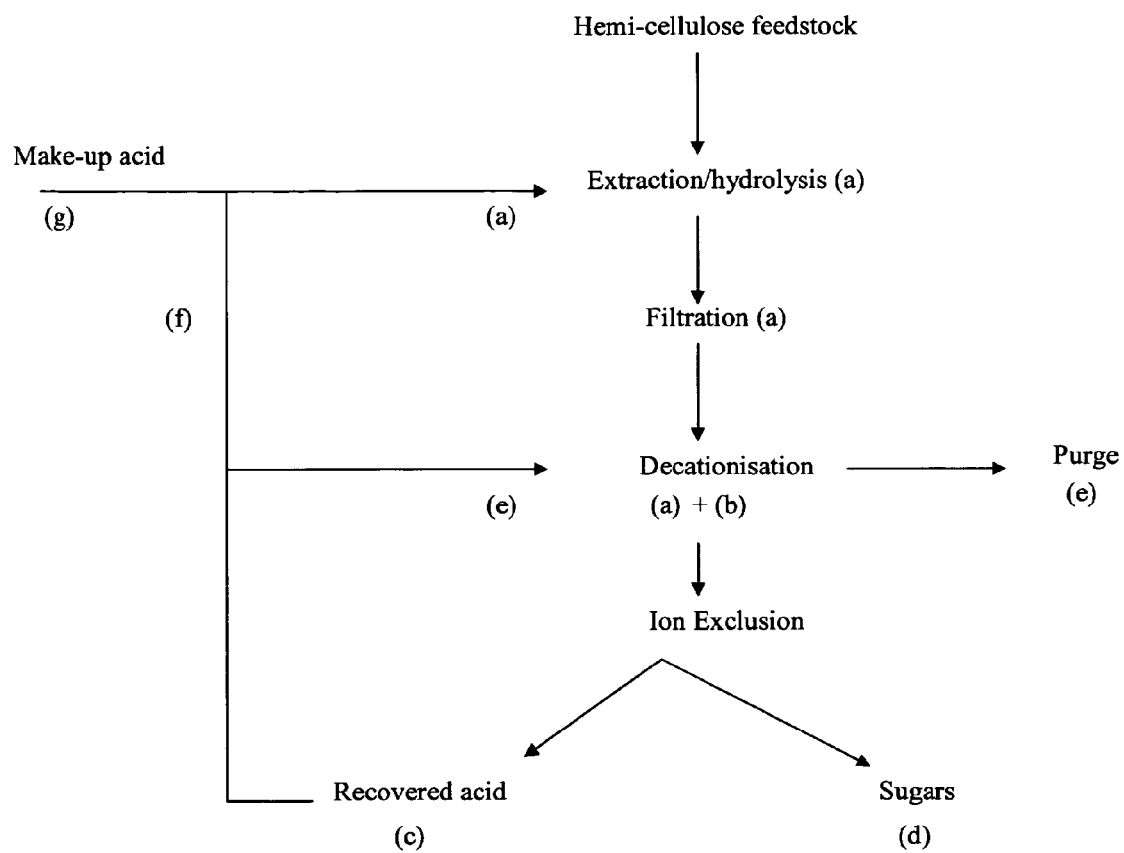
FIG. 1 represents the flow of the acid streams.

In the process according to the invention, ligno-cellulosic substrates, in particular hemicellulose-containing substrates are used. Typical hemicellulose-containing substrates used, are obtained from agricultural and forestry by-products. Hemicellulose hetero-polymers, present along with cellulose in almost all plant cell walls, contain many different sugar monomers including xylose, arabinose, mannose, galactose and rhamnose. Thereby xylose is most of the time the sugar monomer present in the largest amount.

Agricultural by-products suitable as the substrate are a.o. wheat straw, wheat bran, bagasse, corn stover, corn cobs, almond shells, or coconut shells. Forestry by-products can be selected among wood pulping waste such as saw dust, waste wood, or other ligno-cellulosic waste. However, this list should not be considered as limiting, but merely as an illustration.

The initial hydrolysis step is conducted at a pH of from 0.5 to 2, preferably between a pH=1-2. Thereby the reaction temperature may vary between 70° C. and 140° C., preferably between 80° C. and 120° C., and more preferably between 90 and 110° C. Residence time of the substrate will then depend on the pH, reaction temperature and substrate concentration used. Substrate concentration will depend on the type of material processed, but it is typically situated between 5 and 30% d.s. Conditions thus selected are favourable to obtain a maximal extraction yield of soluble hemicellulose monomers and oligomers, and a minimal quantity of degradation products, while at the same time cellulose hydrolysis is limited as much as possible. This hydrolysis step may be conducted in batch or continuously, the last method being preferred. Thereby the acid reagent can be added counter-currently or co-currently.

Counter current extraction can be performed in a diffuser-type reactor as used in the sugar industry or in a screw conveyor reactor. Co-current hydrolysis can be performed in a CSTR equipment. However, the equipment cited above should not be considered as limiting but merely as an illustration.

Most preferred reaction conditions are then:
  pH from 1.1 to 1.6.
  temperature from 90° C. to 100° C.
  substrate concentration from 10% to 25% d.s.
  residence time from 1 to 3 hours, depending on the equipment used.

The acid needed for the partial hydrolysis step is generated from the minerals present in the substrate and which are extracted together with the soluble carbohydrates, from the substrate. Depending on the substrate, different quantities of mineral salts are extracted. These quantities and their compositions are determined by the ash content of these materials but also by the accessibility during extraction. Further details on acid generation are provided hereunder.

In the next step of the process the partially hydrolysed hemicellulose-containing substrate is then separated into the insoluble fraction and a solute containing the dissolved minerals and water-soluble organic material. This soluble material comprises to a major extent xylose or arabinose monomers and oligomers, and some other sugar monomers and oligomers, whose composition is depending on the kind of substrate used.

Separation of these fractions can be realised by means of pressing, centrifugation or filtration techniques, or by combinations thereof. Thereby it is important that the filtrate does not contain suspended material that might cause problems during further processing over the ion exchange resins. Pressing can be realised by means of e.g. screw press or rotary fan press equipments. Centrifugation can be performed by means of self-cleaning disk separators, nozzle separators or separating decanters, separating decanters being preferred. If necessary the decantor overflow can still be treated in a clarifier centrifuge.

Suitable filtration techniques are vacuum filtration, pressure filtration and membrane filtration, including microfiltration and ultrafiltration.

The solid fraction may be washed and pressed, whereby the wash waters can be returned into the hydrolysis reactor. The remaining solid material can be further processed or used as an energy source.

The clarified partial hydrolysates thus obtained contain from 15% to 99% of the pentose sugars present in the raw material. These figures are strongly dependent on the process conditions and the substrates used.

Prior to the decationisation step the clarified partial hydrolysate may be concentrated, if necessary, by evaporation, using standard methods. Typical concentrations aimed at, are about 25-50 d.s. Equipment for evaporation can be selected among plate evaporators, falling film, multiple effect, rising film, or forced circulation evaporators, a falling film evaporator being preferred.

Decationisation can be performed by means of a strong acid cation exchange resin in the $H^+$ form. A macroporous SACE resin as well as gel type SACE resins can be used. Thereby the clarified partial hydrolysate is further acidified through the exchange of cations against protons, and the hydrolysis of oligosaccharides present, may be continued in situ.

The clarified partial hydrolysate is percolated through the ion exchange columns at a velocity of 0.1 to 10 BV/h and at a temperature of between 40 and 99° C. In a more preferred embodiment, decationisation is realised at a temperature of between 40 and 60° C. respectively between 80 and 99° C. (hydrolysis of pentose polymers redundant respectively desirable), and at a percolation speed of 0.5 to 5 BV/h.

The equipment used for decationisation may consist of a two column system or a multi-column system. The two column system uses one column or one set of columns in the operation mode and a second column, or set of columns in the regeneration mode. Preferably a multi-column system is operated in a carrousel mode, whereby one group of columns is regenerated, a second group is used for removal of cations and a third group is used for hydrolysis of remaining pentose polymers.

During this decationisation step minerals extracted from the substrate are transformed into acid, thus providing acid generated from the substrate. At the same time alkali- and earth alkali-metals, heavy metals such as iron or chromium, and nitrogen-containing substances are removed, providing an acid stream low in cations. During start-up of the extraction process fresh acid (so called make-up acid) is used, but eventually almost all acid that is needed for the hydrolysis is recovered from the decationised hydrolysate. The acid present in the hydrolysate is recovered by means of ion exclusion chromatography, and recycled to the hydrolysis reactor except for a small quantity that is used for the regeneration of the decationisation resin. Depending on the concentration of cations in the clarified hydrolysate and on the acid concentration applied for the extraction, the fraction of recovered acid used for regeneration of the decationisation resin may vary between 2 and 40%, more likely between 5 and 10%. The regeneration of the decationisation resin results in a waste stream which is then purged of. This quantity of acid is compensated by a quantity of make-up acid.

As shown in FIG. 1, representing the flow of the acid streams, the quantity of make-up acid (g) needed, corresponds to the quantity lost in the neutral sugars fraction (d)

and the acid used for the regeneration of the decationising resin (e) minus the acid produced by the decationising resin (b). The addition of some make-up acid thereby avoids the build-up of unwanted components in the acid recycle loop. This addition can take place in different locations of the acid recycle loop. One possibility is to introduce the make-up acid together with the recycled acid in the extraction unit. Another possibility consists in introducing the make-up acid at the regeneration of the decationisation resin.

As recycling of acid continues, its composition more and more will correspond to the composition of extractable anions in the hemicellulose feedstock and finally become almost identical to it. This will take a number of cycles, the number being determined by the mineral content in the substrate used, the kind of minerals present and the extraction conditions for obtaining the partial hydrolysate containing the minerals. Typical ash contents for hemicellulose-containing biomass may vary between about 1 to 13%.

Instead of concentrating the clarified partial hydrolysate before the decationisation step, it is also possible to concentrate the decationised hydrolysate before the ion exclusion step. As far as hydrolysis is not complete after extraction and decationisation, further hydrolysis to a solution of mono-saccharides, xylose or arabinos by far being the main component, can then take place during this concentration step.

The ion exclusion unit is operated in a simulated moving bed mode, at a temperature of between 30 and 80° C., a temperature of 40-60° C. being preferred. Resins used for ion exclusion are typically sulphonated polystyrenes with some degree of divinylbenzene (DVB) cross-linking which imparts physical stability to the resin.

The sulphonic acid functionality of the resin particles causes swelling in aqueous media. The resulting microporous resin particles can absorb water and non-ionic solutes. The degree of cross-linking with DVB influences the extent of sorption and prevents total dissolution of the porous resin. Typical cross-linking degrees vary from 2-15% whereby cross-linking degrees of 4-8% are preferred.

The dilute acid stream obtained after ion exclusion is then concentrated before being used in the extraction step.

When necessary, the separated neutral sugars fraction further can be submitted to additional purification steps in order to obtain a pure pentose.

Figure 2:
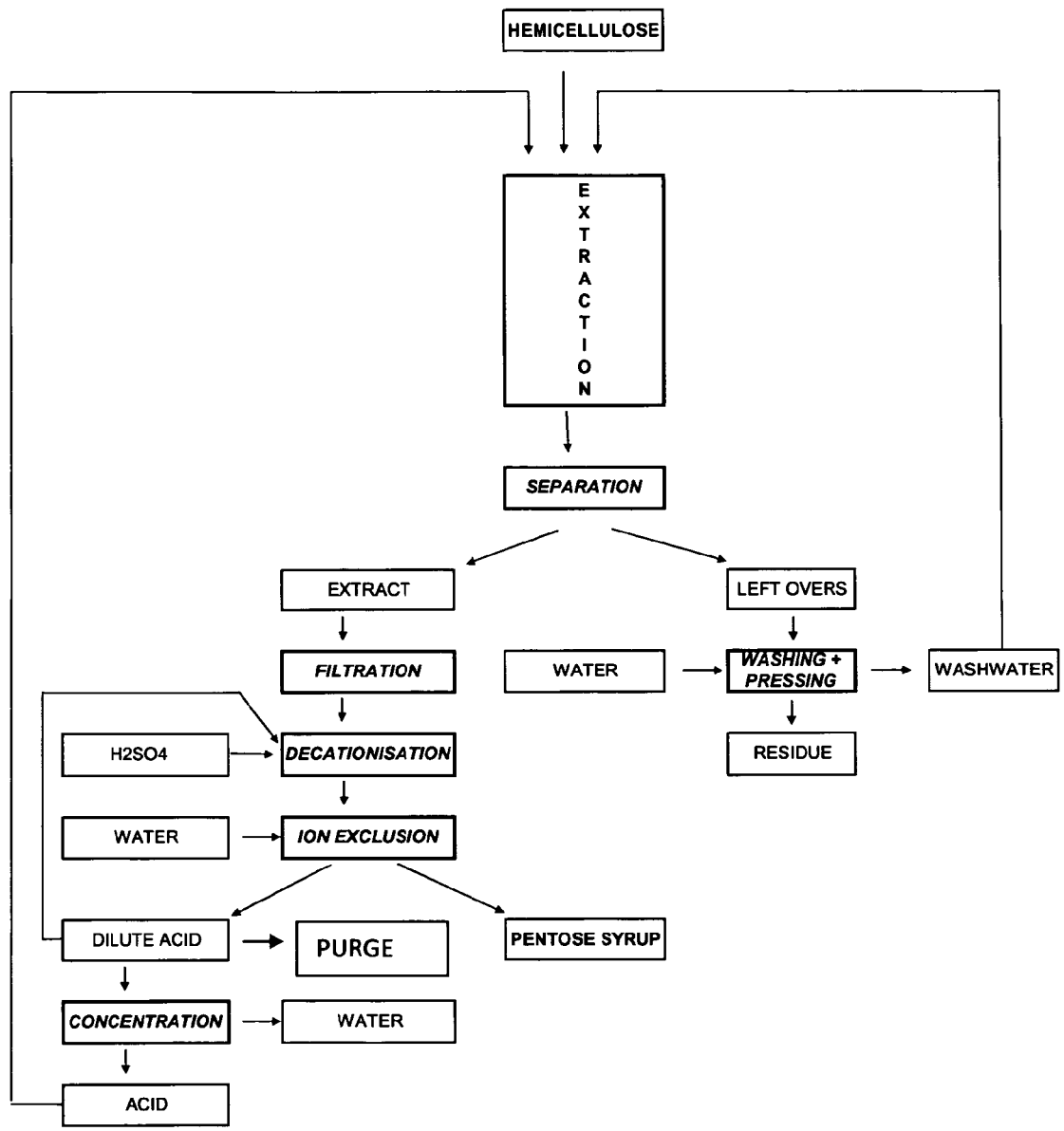
FIG. 2 is a schematically representation of the process according to the invention, wherein the recycled acid is added co-currently.
Figure 3:
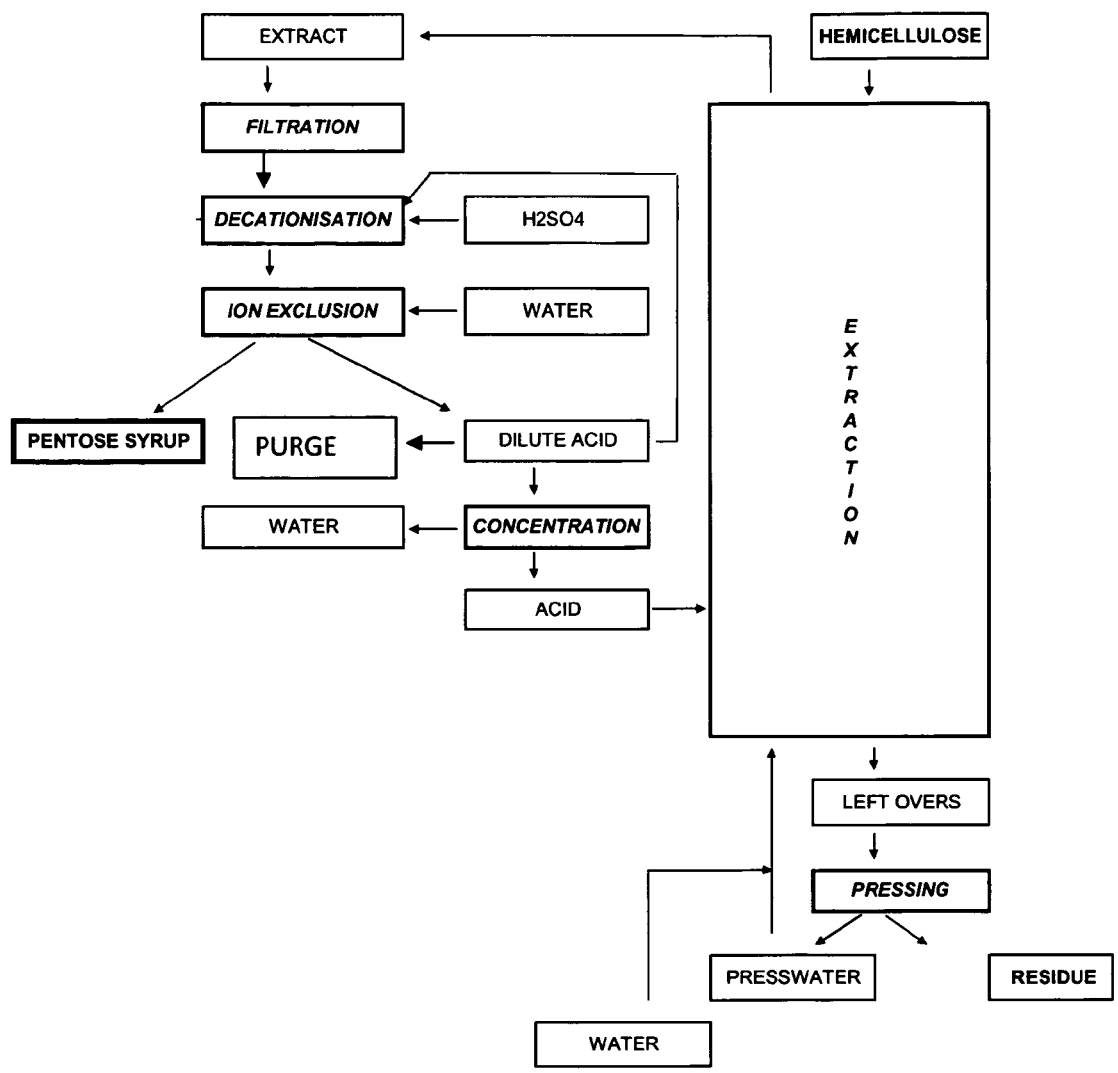
FIG. 3 is a schematically representation of the process according to the invention, wherein the recycled acid is added counter-currently.

The process of the invention is schematically represented in FIGS. 2 and 3

The present invention will further illustrated in the following examples:

Example 1

Sugar cane bagasse (sample obtained via Ercane), EU-Grits (corn cob based, produced by Eurocob), EU-Feeds (corn cob based, produced by Eurocob), sugar beet pulp (sample from the Tereos sugar beet plant at Chevrières, France) and wheat bran (sample taken from the wheat mill in the Tereos Syral plant in Aalst, Belgium) have been analysed for extractable cations. Therefore, aliquot's of these products were suspended in demineralised water in order to obtain slurries at 5% dry solids by weight.

The suspensions were heated to 99° C. and kept at that temperature while stirred for 4 hours. After that, the samples were cooled down to ambient temperature and filtered through a card board filter to remove suspended solids. The filtrates were further analysed for mineral cations, the results are given in table 1.

TABLE 1 water extractable cations in various hemicelluloses feedstocks

| Substrate | ppm in extract | | | | meq/kg ds feed | | | | |
|---|---|---|---|---|---|---|---|---|---|
| | Na | K | Mg | Ca | Na | K | Mg | Ca | total |
| Bagasse | 2.7 | 24 | 12 | 23 | 2.3 | 12 | 20 | 23 | 58 |
| EU-Grits* | 2.1 | 373 | 3.3 | 0.5 | 1.8 | 191 | 5.5 | 0.5 | 198 |
| EU-Feeds* | 1.5 | 408 | 11 | 4.9 | 1.3 | 208 | 17 | 4.9 | 232 |
| Sugar beet pulp | 7.9 | 96 | 36 | 144 | 6.8 | 49 | 60 | 144 | 259 |
| Wheat bran | 6.1 | 775 | 272 | 24 | 5.3 | 396 | 447 | 24 | 873 |

*product obtained by milling of corn cob part and classification of the milled product, produced by Eurocob Example 2

EU-Grits was suspended in demineralised water in the ratio needed to get a slurry at 12% dry solids by weight. Sulphuric acid was added up to 5% on dry EU-Grits basis. The acidified slurry was heated to 99° C. and kept at that temperature for 6 hours while gently stirring.

The slurry was then cooled down to ambient temperature and the remaining undissolved fibre fraction was separated on a cardboard depth filter (type T 1000 supplied by Pall Corporation). The filtrate was further decationised by passing it at 1 bv/h over a column filled with Dowex Marathon C resin (gel type SACE resin) in the H+ form resulting in a decationised EU-Grits extract.

The separation of acid and sugars was then tried for in an ion exclusion mode. Therefore, 500 ml of DOWEX* MONOSPHERE* N279 (gel type SACE resin) in the H+ form, was filled into a jacketed chromatography column (GE Healthcare, Type C 26/100). For conditioning of the resin, 10 l of decationised EU-Grits extract was percolated through the column at 50° C. and 1 bv/h. After that, the column was rinsed with 3 bv demineralised water at 50° C. and 1 bv/h.

Figure 4:
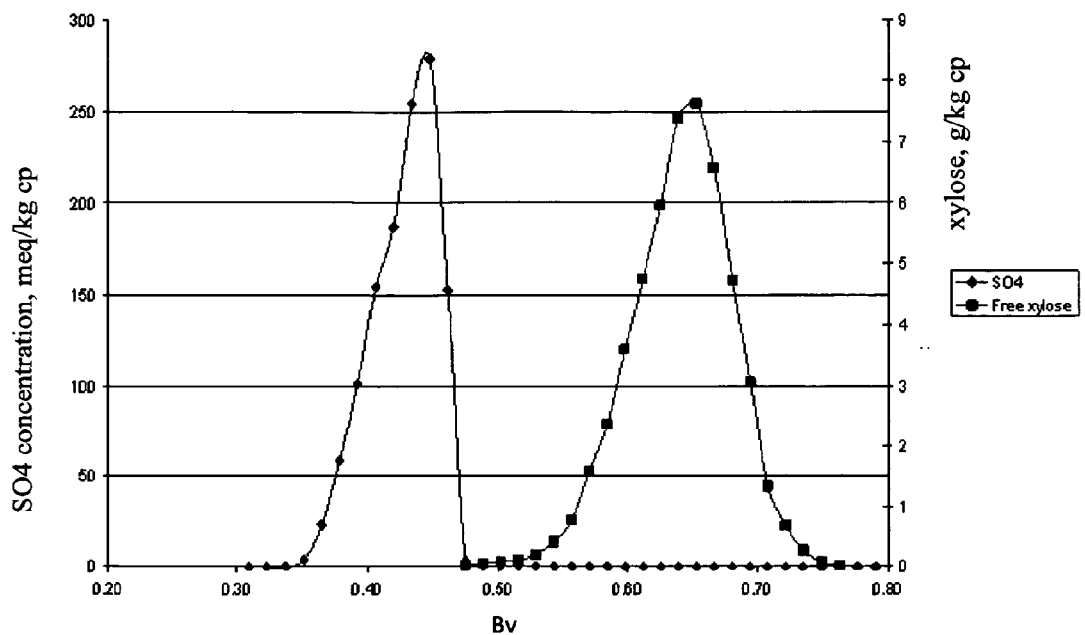
FIG. 4 shows the results of the ion exclusion of the decationised EU-Grits hydrolysate (see example 2). The sulphate, origination from the sulphuric acid applied for the extraction, and the free (monomeric) xylose produced during the extraction, are well separated.

The acid/sugar separation was now evaluated by first bringing 20 ml of decationised EU-Grits extract on the top of the column and then eluting with demineralised water at 50° C. and 1 bv/h. Fractions of ~10 ml each were collected at the outlet of the column and individually analysed for sulphate and free xylose The results in FIG. 4 show two well separated peaks.

Example 3

Wheat bran was suspended in demineralised water in the ratio needed to get to slurry at 12% dry solids by weight. Sulphuric acid was added up to 5% on dry wheat bran basis. The acidified slurry was heated to 99° C. and kept at that temperature for 6 hours while gently stirring.

The slurry was then cooled down to ambient temperature and the remaining undissolved fibre fraction was separated on a cardboard depth filter (type T 1000 supplied by Pall Corporation). The filtrate was further decationised by passing it at 1 bv/h over a column filled with Dowex Marathon C resin (gel type SACE resin) in the H+ form resulting in a decationised wheat bran extract.

The separation of acid and sugars was then tried for in an ion exclusion mode. Therefore, 500 ml of DOWEX* MONOSPHERE* N279 (gel type SACE resin) in the H+ form, was filled into a jacketed chromatography column (GE Healthcare, Type C 26/100). For conditioning of the resin, 10 l of decationised wheat bran extract was percolated through the column at 50° C. and 1 bv/h. After that, the column was rinsed with 3 bv demineralised water at 50° C. and 1 bv/h.

Figure 5:
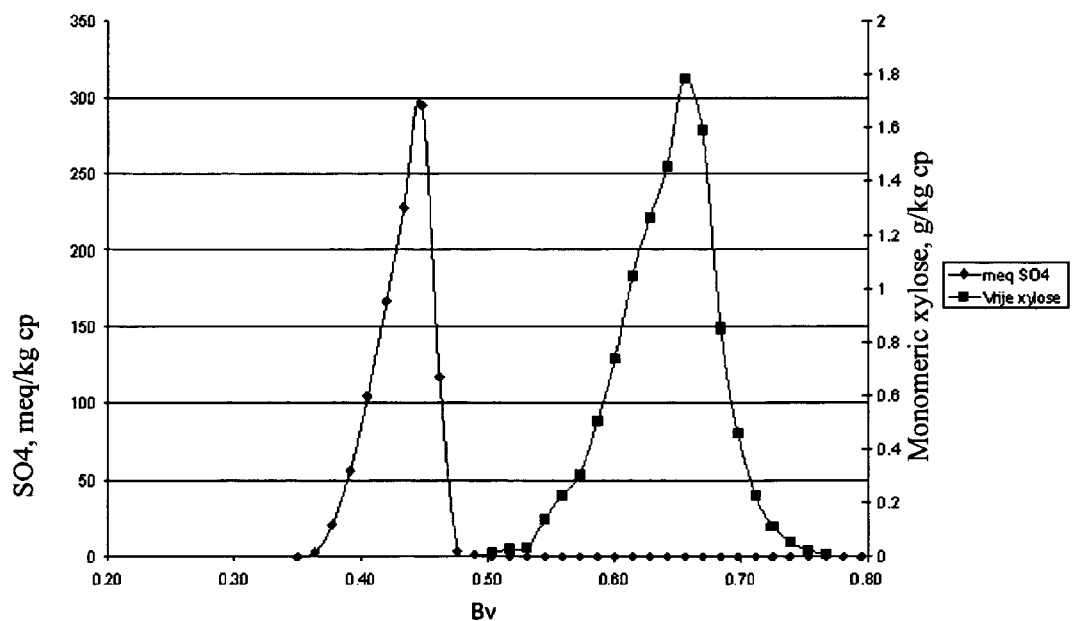
FIG. 5: the results of the ion exclusion of the wheat bran hydrolysate (see example 3). The sulphate, origination from the sulphuric acid applied for the extraction, and the free (monomeric) xylose produced during the extraction, are well separated.

The acid/sugar separation was now evaluated by first bringing 20 ml of decationised wheat bran extract on the top of the column and then eluting with demineralised water at 50° C. and 1 bv/h. Fractions of ~10 ml each were collected at the outlet of the column and individually analysed for sulphate and free xylose The results in FIG. 5 show two well separated peaks.

Example 4

Sugar cane bagasse was suspended in demineralised water in the ratio needed to get to slurry at 12% dry solids by weight. Sulphuric acid was added up to 5% on dry bagasse basis. The acidified slurry was heated to 99° C. and kept at that temperature for 6 hours while gently stirring.

The slurry was then cooled down to ambient temperature and the remaining undissolved fibre fraction was separated on a cardboard depth filter (type T 1000 supplied by Pall Corporation). The filtrate was further decationised by passing it at 1 bv/h over a column filled with Dowex Marathon C resin (gel type SACE resin) in the H+ form resulting in a decationised bagasse extract.

The separation of acid and sugars was then tried for in an ion exclusion mode. Therefore, 500 ml of DOWEX* MONOSPHERE* N279 (gel type SACE resin) in the H+ form, was filled into a jacketed chromatography column (GE Healthcare, Type C 26/100). For conditioning of the resin, 10 l of decationised bagasse extract was percolated through the column at 50° C. and 1 bv/h. After that, the column was rinsed with 3 bv demineralised water at 50° C. and 1 bv/h.

The acid/sugar separation was now evaluated by first bringing 20 ml of decationised bagasse extract on the top of the column and then eluting with demineralised water at 50° C. and 1 bv/h. Fractions of ~10 ml each were collected at the outlet of the column and individually analysed for Bx and conductivity. A selection of fractions also was analysed for xylose content.

Figure 6:
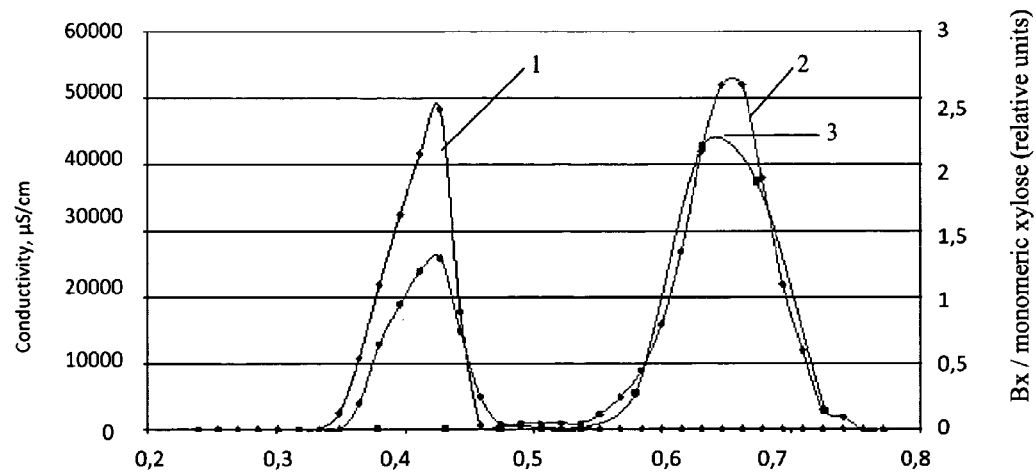
FIG. 6: the results of the ion exclusion of the decationised bagasse hydrolysate (see example 4). The acid applied for the extraction is eluting in a first peak characterised by a high conductivity and Brix and absence of monomeric xylose. The monomeric xylose produced during the extraction is eluting in a second peak characterised by a high Brix and high concentration of xylose and a low conductivity. Both peaks are well separated.

The results in FIG. 6 show two well separated peaks. The first one, high in Bx and conductivity, represents the elution of acid. The second one, high in Bx yet low in conductivity, represents the elution of sugars. The results for xylose analysis confirm there is no monomeric xylose eluting with the acid.

Comparative Example 5

This example, not being part of the invention, shows the effect of the absence of a decationisation step, on the separation of acid and sugars. (see FIG. 7)

Sugar cane bagasse was suspended in demineralised water in the ratio needed to get to slurry at 12% dry solids by weight. Sulphuric acid was added up to 5% on dry bagasse basis. The acidified slurry was heated to 99° C. and kept at that temperature for 6 hours while gently stirring.

The slurry was then cooled down to ambient temperature and the remaining undissolved fibre fraction was separated on a decanter device. To complete the separation, the overflow of the decanter was then filtered through a cardboard depth filter (type T 1000 supplied by Pall Corporation). The filtrate was not decationised.

The separation of acid and sugars was then tried for in an ion exclusion mode. Therefore, 500 ml of DOWEX* MONOSPHERE* N279 (gel type SACE resin) in the H+ form, was filled into a jacketed chromatography column (GE Healthcare, Type C 26/100). For conditioning of the resin, 10 l of non decationised bagasse extract was percolated through the column at 50° C. and 1 bv/h. After that, the column was rinsed with 3 bv demineralised water at 50° C. and 1 bv/h.

The acid/sugar separation was now evaluated by first bringing 20 ml of non decationised bagasse extract on the top of the column and then eluting with demineralised water at 50° C. and 1 bv/h. Fractions of ~10 ml each were collected at the outlet of the column and individually analysed for Bx and conductivity. A selection of fractions also was analysed for xylose content.

Figure 7:
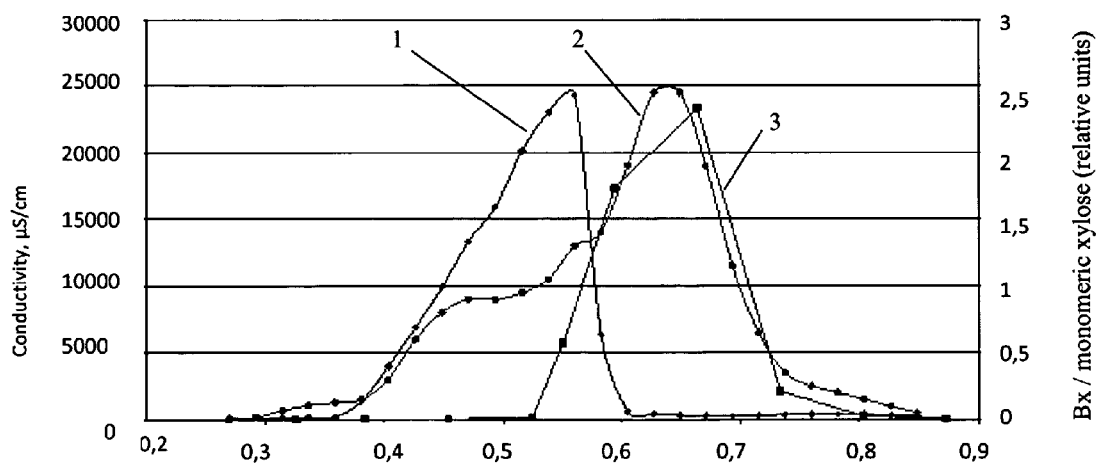
FIG. 7: the results of the ion exclusion of the non decationised bagasse hydrolysate (see example 5). The acid applied for the extraction is eluting in a first peak characterised by a high conductivity and Brix. The monomeric xylose produced during the extraction is eluting in a second peak characterised by a high Brix and high concentration of xylose. The Brix doesn't decrease in between the conductivity and xylose peak. There is also some xylose eluting while the conductivity is still high. It means the acid and xylose peaks are poorly separated. This will result in a loss of xylose in the recycled acid and/or a higher refining cost for the separated xylose.

The results in FIG. 7 show two incompletely separated peaks. In between the fraction with the highest conductivity and the one with the highest Bx, there is no fraction with low conductivity and low Bx. The results for xylose analysis confirm there is monomeric xylose eluting under the (high conductivity) acid peak.

The invention claimed is:

1. Process for extraction of pentose from a ligno-cellulose containing substrate, characterised in that the process comprises the steps of:
   submitting the ligno-cellulose containing substrate to an acidic partial hydrolysis step in a hydrolysis reactor;
   separating the partially hydrolysed ligno-cellulose substrate into an insoluble fraction and a liquid fraction comprising dissolved minerals and water-soluble organic material;
   submitting the liquid fraction to a decationisation step, wherein said liquid fraction is sent over a strong-acid cation exchange (SACE) resin in the hydrogen form;
   subsequently sending the decationised liquid fraction over a strong-acid cation exchange (SACE) resin working in an ion exclusion mode, wherein acid and neutral monomelic sugars are separated from each other; and
   recycling at least a part of the acid to the hydrolysis reactor;
   wherein said acidic partial hydrolysis step is conducted at a pH of from 0.5 to 2; and
   wherein prior to the decationisation step, said liquid fraction is concentrated until about 25-50% d.s.

2. Process according to claim 1, characterised in that in said acidic partial hydrolysis step, the reaction temperature varies between 70° C. and 140° C.

3. Process according to of claim 1, characterised in that the said acidic partial hydrolysis step is conducted in batch or continuously.

4. Process according to claim 3, characterised in that in a continuously performed hydrolysis step, the recycled acid is added counter-currently or co-currently to the hydrolysis reactor.

5. Process according to claim 1, characterised in that the separated insoluble fraction is further washed and pressed, wherein wash water is returned into the hydrolysis reactor.

6. Process according to claim 1, characterised in that said liquid fraction is sent over a SACE resin working in a decationisation mode, at a velocity of 0.1 to 10 BV/h and at a temperature of between 40° C. and 99° C.

7. Process according to claim 1, characterised in that the SACE resin, working in a decationisation mode, is regenerated using a part of the acid obtained during the ion exclusion step.

8. Process according to claim 1, characterised in that make-up acid is added to the hydrolysis reactor and/or used for the regeneration of the SACE resin, working in a decationisation mode.

* * * * *